July 24, 1973 F. J. MELGES Re. 27,710

NON-WOVEN SURGICAL SHIELD OR COVER MEMBER

Original Filed Feb. 14, 1967 2 Sheets-Sheet 1

INVENTOR

FREDERICK J. MELGES

BY Roy A. Plant

ATTORNEY

NON-WOVEN SURGICAL SHIELD OR COVER MEMBER

Original Filed Feb. 14, 1967 2 Sheets-Sheet 2

INVENTOR
FREDERICK J. MELGES
BY Roy A. Plant
ATTORNEY

United States Patent Office

Re. 27,710
Reissued July 24, 1973

27,710
NON-WOVEN SURGICAL SHIELD OR COVER MEMBER

Frederick J. Melges, 314 N. Orchard Place,
Battle Creek, Mich. 49017

Original No. 3,503,391, dated Mar. 31, 1970, Ser. No. 616,128, Feb. 14, 1967. Application for reissue Aug. 2, 1971, Ser. No. 168,503
Int. Cl. A61f *13/00*
U.S. Cl. 128—132 D 10 Claims

Matter enclosed in heavy brackets [ ] appears in the original patent but forms no part of this reissue specification; matter printed in italics indicates the additions made by reissue.

ABSTRACT OF THE DISCLOSURE

The non-woven surgical shield or cover member which carries improvements in the form of special reinforcement, adhesive anchoring means, multiple compartment instrument holding pocket members, supply carrying pockets, waterproofing, special construction of the surgical opening, and a rough surfaced reinforcing member near but spaced from surgical opening.

The present invention deals broadly with hospital operating room supplies and more specifically with improved disposable drapes for use in various surgical operations as well as obstetrics.

In preparing for operations requiring a lithotomy position of the patient, gynecological, and other operations in addition to obstetrics, the patient may be either placed on an operating or delivery table with the legs elevated and the feet supported in stirrups (lithotomy position), or supinely in position for other types of operations such as appendectomy, gal bladder removal, hysterectomy, colostomy, breast surgery, and the like. The common practice up until recently has been to drape the table with a sterile linen sheet, and then separately drape the patient with various sizes of sterile linen sheets so as to cover the patient for sterile purposes preventing contamination as well as for warmth during the operation and yet expose the operation or treatment area between the side edges of the covering linen sheets. These linen sheets in use become bloodstained and require laundering between operations or obstetrical use, and then autoclaving for sterilization. This caused a bottleneck, particularly on weekends when the laundry was closed, and as well required an expensive linen inventory. Moreover, bloodstains on linens are substantially impossible of complete removal while forming a starting point for the growth of bacteria and virus components when next brought into contact with same. Still further, various germs, bacteria, and virus components readily passed through linens, particularly when wet, which in combination with the distasteful work of laundering soiled operating and obstetrical room linens made the finding of substitute disposable non-woven linen-like materials a desired necessity. My U.S. Pat. Nos. 3,030,957; 3,037,507; and 3,251,360 formed the starting point of providing disposable draping sheets and other members which have been standardizing and revolutionizing the obstetrical and surgical procedures. The present invention relates to further improvements in this field of patient draping which overcomes some of the technical difficulties encountered such as the slipping of the drapery components during the use of such drapery components under obstetrical and surgical conditions. It was a complete lack of anything on the open market for overcoming these difficulties which led to the conception and development of the present invention.

Accordingly, among the objects of the present invention is the provision of improved non-woven disposable surgical and obstetrical draping components which overcome the slipping and other difficulties inherent in patient draping procedures including the use of old style linen drapes formerly in exclusive use in the field.

Another object of this invention is to provide instrument and supplies holding means as part of the improved non-woven disposable drapes.

Another object is to provide a roughened and reinforced area on the upper face of the drape for the reception of used surgical instruments or even a newly delivered baby in obstetrical work.

Still further objects and advantages of the present invention will appear as the description proceeds.

To the accomplishment of the foregoing and related ends, the invention, then, consists of the improved drape means hereinafter fully described and particularly pointed out in the claims, the annexed drawings and the following description setting forth in detail certain means for carrying out the invention, such disclosed means illustrating, however, but one of various ways in which the principle of the invention may be used.

Figure 1:
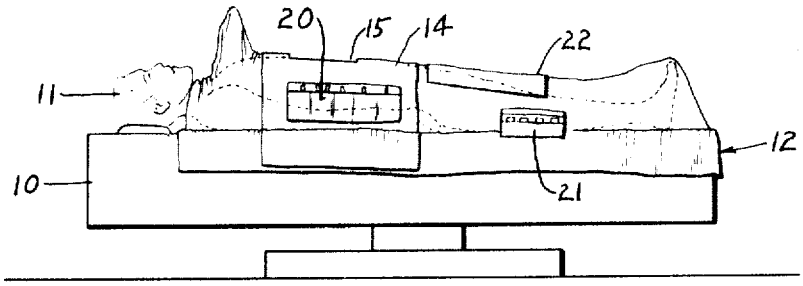
FIG. 1 shows a side view of a patient on an operating table draped in accordance with the present invention.
Figure 2:
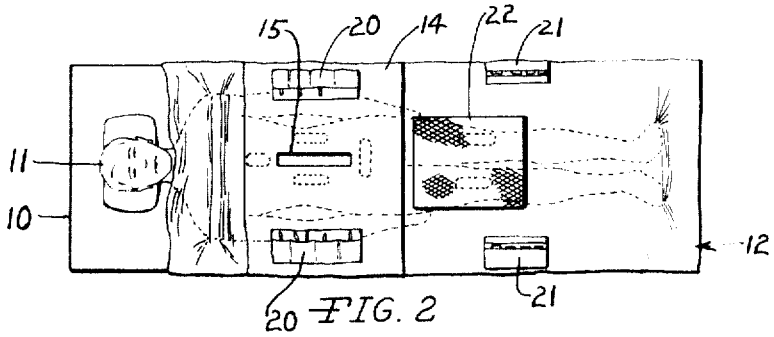
FIG. 2 shows a top view of the assembly of table, patient and draping illustrated in FIG. 1.

Referring more particularly to FIGS. 1 and 2 of the drawings, it will be noted that there is shown an operating or delivery table 10 on which a patient 11 is shown in supine position which is used for many different types of operations, and covered with one form of the present improved drapes 12, which may be broadly referred to as a surgical drape, and which will be hereinafter described in detail.

Figure 3:
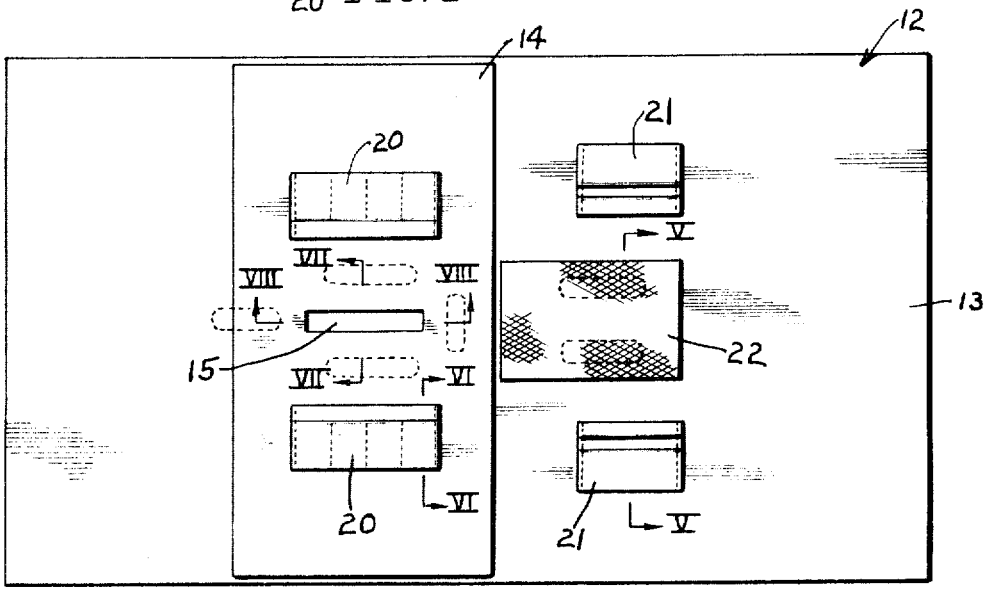
FIG. 3 shows an enlarged top view of the improved drape shown in use in FIGS. 1 and 2.
Figure 4:
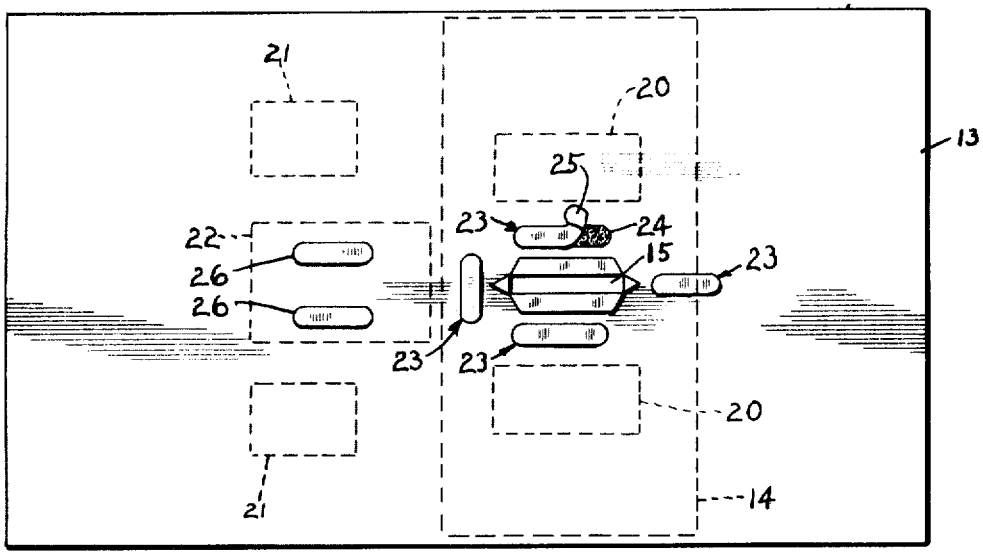
FIG. 4 shows the opposite or underside of the improved drape illustrated in FIG. 3.
Figure 5:
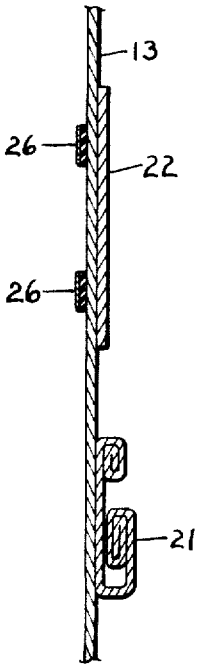
FIG. 5 shows an enlarged sectional view as taken along the line V—V of FIG. 3, looking in the direction of the arrows and with the material being shown of exaggerated thickness for ease of illustration.
Figure 6:
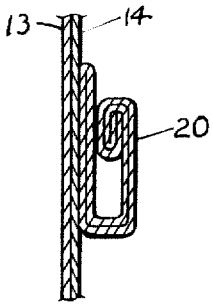
FIG. 6 shows an enlarged sectional view as taken along line VI—VI of FIG. 3, looking in the direction of the arrows, and with the material being shown of exaggerated thickness.

The surgical drape 12 can be made of one piece as illustrated in FIGS. 3 and 4, although the improvements hereinafter described are applicable to other forms of this drape, even to multiple piece drapes, and it is intended that the showing be considered as diagrammatically illustrating other forms of surgical drapes incorporating the special features which will be hereinafter described in detail and illustrated in the drawings.

Referring now to FIGS. 3 and 4, the particular surgical drape 12 illustrated has a main sheet 13 formed from soft water-resistant non-woven material which is reinforced and forms a barrier substantially preventing the passage therethrough of infectious organisms even though blood or other operating fluids may pass therethrough. One form of this non-woven material may also include treatment with plastic to make same completely resistant or impervious to the passage of blood or other operating fluids therethrough while remaining soft to the touch, and in another form the material may be laminated so that the plastic layer would have the non-woven material on at least one if not both faces so as to provide the linen-like feeling.

The present invention is aimed at obviating the use of woven materials, commonly called "linens" in connection with surgery and obstetrics, and to use in the place of same suitable replacement items in the form of disposable non-woven material which can be generally referred to as a cellulose fabric, and in a sense can be called "paper" in some forms. This material, as hereinafter set forth, is preferably moderately soft, relatively strong and tear resistant, is relatively strong when wet, and may be self-reinforced by means of reinforcing threads such as "nylon" or the like. Such material is also a relatively good filter so that bacteria and even virus carried by operating and obstetrical liquids, in addition to blood, will be filtered out. Also by treating this material with a suitable plastic same can be kept soft to the touch and at the same time form a barrier to passage of liquids containing bacteria, or virus through same. Paper is made in many forms with or without self-reinforcement and the term "paper" may be used to indicate this special non-woven material which has been used in many tests and proven satisfactory for carrying out the invention.

Figure 7:
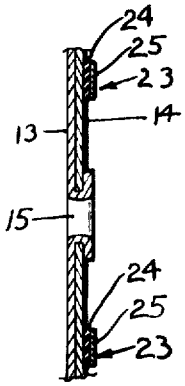
FIGS. 7 and 8 show enlarged sectional views of the surgical opening in the drape of FIG. 3, as taken respectively along lines VII—VII and VIII—VIII of same, looking in the direction of the arrows, with the material being of exaggerated thickness.
Figure 8:
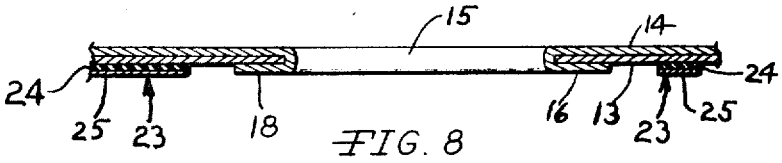

Main sheet 13 in the operating area is preferably reinforced full width for instance by means of a substantially rectangular reinforcing member 14 which may be of the same kind of material as main sheet 13, and adhesively or otherwise fastened to the latter. A surgical opening 15 is formed in the portion of main sheet 13 at the desired operating point reinforced by reinforcing member 14. This surgical opening 15 is preferably rectangular as shown, with main sheet 13 having the opening cut out while the reinforcing member 14 is cut centrally lengthwise with V-notch ends to form four flaps 16, 17, 18 and 19, FIG. 4, which are pushed through opening 15 in main sheet 13 and preferably adhesively fastened in the position shown in FIGS. 4, 7, and 8, thus producing a smooth sided surgical opening 15.

During the course of an operation the surgeon needs some place to conveniently hold the surgical instruments so that they will be handy of access and not become contaminated from touching non-sterile surfaces. The present invention takes care of this by providing multiple pocket members 20, FIGS. 1, 2, 3 and 6, at opposite sides of surgical opening 15. The individual pockets of these pocket members 20 hold the instruments upright ready for the surgeon to retrieve them whenever needed.

The surgeon also needs some handy place to keep supplies in the form of pieces of catgut, clamps, needles, et cetera, ready for immediate use and this is taken care of by means of supply pockets 21, FIGS. 1, 2, 3 and 5 at opposite sides of the rough surfaced reinforcing member 22. The latter member 22 serves as a semi-nonskid point where the surgeon can toss his instruments which he no longer needs for the operation. If desired, this rough surfaced reinforcing member 22 can have magnetized metal incorporated in same to better hold the metal instruments delivered to same. Also in obstetrics this rough surfaced reinforcing member may be located over the mother's stomach and serve as a point where the newly born baby can be placed while the umbilical cord is clamped or tied and the baby is preliminarily cleaned up.

One of the most irritating things to a surgeon is to have the surgical drape of any type slip out of position so that the surgical opening 15 no longer corresponds with the incision point of the patient. To overcome this the surgical drape 12 may be provided with adhesive members 23 adapted to be stuck to the patient and thus prevent slippage of the drape 12. One convenient way to accomplish this is to provide double faced adhesive tape 24 with one side of same adhesively fastened to the underside of the main sheet 13 on opposite sides of surgical opening 15 while covering the exposed adhesive surface with waxed paper or the like 25 having low adhesive attraction to facilitate peeling off this covering waxed paper or the like when the drape is in place and ready for adhesively fastening. To still further anchor the surgical drape 12 in place same may be additionally provided with adhesive members 26 which may be on the underside of main sheet 13 below rough surfaced member 22, as shown in FIG. 4. These adhesive members would also be provided with the waxed paper cover member 25 as previously described.

With these adhesive members in place, the surgical drape 12 in sterilized form would be placed over the patient in desired position for the operation and then the waxed paper cover members 25 for the adhesive would be peeled off and the exposed adhesive areas would then be pressed down to adhesively anchor the surgical drape 12 in place so as to avoid slippage under operating conditions. If the drape needs shifting, same way be pulled up in the adhesively fastened points and then after shifting to the desired new position it can be pressed down again to hold same fixedly in the new position. Instead of using double faced adhesive tape the adhesive may be coated directly on the underface of the drape and then covered with the waxed paper or the like. Another alternate adhesive holding means would involve placing adhesive of suitable type in desired location on the patient and in matching location on the underface of the drape and drying these surfaces so that they do not feel particularly sticky yet when the two adhesive coated surfaces are brought together they will stick to each other to hold the surgical drape in place.

It will be seen from the above that simple and relatively expensive yet practical and durable means have been disclosed for attaining the desired ends. Attention is invited, however, to the possibility of making variations within the spirit and scope of the invention set forth. Also directional terms have been used to facilitate explaining the invention in the position shown in the drawings and are not to be considered as limiting the invention.

Other modes of applying the principles of my invention may be employed, instead of those explained, change being made as regards the cover member and its combinations herein disclosed, provided the means and features stated by any of the following claims or the equivalent of such stated means and features be employed.

I therefore particularly point out and distinctly claim as my invention:

1. A surgical drape of the character described for use over a patient which comprises a main sheet formed of a non-woven cellulose fabric which is self-reinforced and strong when wet, a substantially rectangular reinforcing member fastened crosswise of same, said main sheet and reinforcing member having an operating opening therethrough, and means for anchoring said sheet to said patient so as to hold said sheet in fixed position, wherein said means for anchoring said sheet to said patient is in the form of at least one adhesive member adjacent said operating opening and on the underside of said main sheet in position to contact and adhere to said patient, wherein said operating opening is smooth faced due to one of said members in the form of the main sheet and its reinforcing sheet saving an opening cut in same in the desired operating area, while the other is slit lengthwise of of said opening to form four flaps which are pushed through said opening in the other sheet and turned back, and means for anchoring said flaps in place, and wherein said crosswise extending reinforcing member having said operating opening therethrough also has at least one pocket means adjacent but spaced sidewise of said main sheet from said operating opening, said pocket means being adapted to hold instruments, wherein said main sheet also has at a point located lengthwise of same and adjacent but spaced from said operating opening a second reinforcing member which has a rough semi-nonskid upper surface and means for fastening said second reinforcing means to the top face of said main sheet.

[2. A disposable sterile shield or cover member for surgical, obstetrical, lithotomy, or other uses, comprising a main sheet of non-woven material broadly known as a cellulose fabric, and which is moderately soft, relatively strong and tear resistant, as well as strong when wet, and resistant to the passage of bacteria, germs, and virus therethrough even though carried by blood, operating fluids, or other liquids, wherein said sheet is also self-reinforced and has a plastic liquid barrier incorporated in same to prevent the passage of liquids through same thus making it waterproof while having liquid absorbing capabilities.]

3. [A disposable sterile shield or cover member as set forth in claim 2] *A disposable sterile shield or cover member for surgical, obstetrical, lithotomy, or other uses, comprising a main sheet of non-woven material broadly known as a cellulose fabric, and which is moderately soft, relatively strong and tear resistant, as well as strong when wet, and resistant to the passage of bacteria, germs, and virus therethrough even though carried by blood, operating fluids, or other liquids, wherein said sheet is also self-reinforced and has a plastic liquid barrier incorporated in same to prevent the passage of liquids through same thus making it waterproof while having liquid absorbing capabilities,* wherein said sheet has a reinforcing member extending crosswise of same, means for anchoring same to said main sheet, said main sheet in the area covered by said reinforcing member having a pre-formed operating opening extending completely through both said main sheet and reinforcing member.

4. A disposable sterile shield or cover member for surgical, obstetrical, lithotomy, or other uses, comprising a main sheet of non-woven material broadly known as a cellulosic fabric, and which is moderately soft, relatively strong and tear resistant, as well as strong when wet, and resistant to the passage of bacteria, germs, and virus therethrough even though carried by blood, operating fluids, or other liquids, wherein said sheet is also self-reinforced and has a plastic liquid barrier incorporated in same to prevent the passage of liquids through same thus making it waterproof while having liquid absorbing capabilities, and wherein said sheet has a reinforcing member extending crosswise of same, means for anchoring same to said main sheet, said main sheet in the area covered by said reinforcing member having an operating opening extending completely through both said main sheet and reinforcing member.

5. [A disposable sterile shield or cover member as set forth in claim 2] *A disposable sterile shield or cover member for surgical, obstetrical, lithotomy, or other uses, comprising a main sheet of non-woven material broadly known as a cellulose fabric, and which is moderately soft, relatively strong and tear resistant, as well as strong when wet, and resistant to the passage of bacteria, germs, and virus therethrough even though carried by blood, operating fluids, or other liquids, wherein said sheet is also self-reinforced and has a plastic liquid barrier incorporated in same to prevent the passage of liquids through same thus making it waterproof while having liquid absorbing capabilities,* wherein said sheet has reinforcing member extending crosswise of same, means for anchoring same to said main sheet, said main sheet in the area covered by said reinforcing member having an operating opening extending completely through both said main sheet and reinforcing member, and wherein said main sheet of non-woven material has means on its underside spaced from said operating opening for adhesively fastening same to the patient on whom same is to be used, to hold the surgical opening through said cover member in fixed operating position throughout the conducting of an operation.

6. A disposable sterile shield or cover member for surgical, obstetrical, lithotomy, or other uses, comprising a main sheet of non-woven material broadly known as a cellulose fabric, and which is moderately soft, relatively strong and tear resistant, as well as strong when wet, and resistant to the passing of bacteria, germs, and virus therethrough even though carried by blood, operating fluids, or other liquids, wherein said sheet is also self-reinforced and has a plastic liquid barrier incorporated in same to prevent the passage of liquids through same thus making it waterproof while having liquid absorbing capabilities, wherein said sheet has a reinforcing member extending crosswise of same, means for anchoring same to said main sheet, said main sheet in the area covered by said reinforcing member having an operating opening extending completely through both said main sheet and reinforcing member, wherein said main sheet of non-woven material has means on its underside for adhesively fastening same to the patient on whom same is to be used, to hold the surgical opening through said cover member in fixed operating position throughout the conducting of an operation, and wherein said means for adhesively fastening said cover member to the patient is in the form of adhesive applied directly to the underside of said main sheet of non-woven material, and a peelable strip shielding said adhesive, whereby said cover member can be accurately fitted over the patient, said peelable strip removed and the cover member fastened to the patient by said exposed adhesive.

7. [A disposable sterile shield or cover member as set forth in claim 2] *A disposable sterile shield or cover member for surgical, obstetrical, lithotomy, or other uses, comprising a main sheet of non-woven material broadly known as a cellulose fabric, and which is moderately soft, relatively strong and tear resistant, as well as strong when wet, and resistant to the passage of bacteria, germs, and virus therethrough even though carried by blood, operating fluids, or other liquids, wherein said sheet is also self-reinforced and has a plastic liquid barrier incorporated in same to prevent the passage of liquids through same thus making it waterproof while having liquid absorbing capabilities,* wherein said cover member has in its reinforced portion containing said surgical opening, and at opposite sides of the latter, pocket members for surgical instruments, and means for fastening said pocket members to said reinforced portion of said cover member.

8. [A disposable sterile shield or cover member as set forth in claim 2] *A disposable sterile shield or cover member for surgical, obstetrical, lithotomy, or other uses, comprising a main sheet of non-woven material broadly known as a cellulose fabric, and which is moderately soft, relatively strong and tear resistant, as well as strong when wet, and resistant to the passage of bacteria, germs, and virus therethrough even though carried by blood, operating fluids, or other liquids, wherein said sheet is also self-reinforced and has a plastic liquid barrier incorporated in same to prevent the passage of liquids through same thus making it waterproof while having liquid absorbing capabilities,* wherein spaced lengthwise of said cover member from said first reinforced area containing said surgical opening is a second reinforcing member which has a rough semi-nonskid upper surface, and means for fastening said second reinforcing means to said cover member.

9. A disposable sterile shield or cover member as set forth in claim 4, wherein said second reinforcing member which has a rough semi-nonskid upper surface, has incorporated therein magnetized metal means for magnetically attracting surgical instruments formed of steel when placed thereon.

10. A disposable sterile shield or cover member as set forth in claim 4, wherein there is at opposite sides of said second reinforcing member supply holding pockets, and means for fastening same to said cover member.

11. A disposable sterile shield or cover member as set forth in claim 6, wherein all of said fastening means for fastening reinforcing parts and pockets on said cover member, are in the form of adhesive.

References Cited

The following references, cited by the Examiner, are of record in the patented file of this patent or the original patent.

UNITED STATES PATENTS

| | | | |
|---|---|---|---|
| 3,310,459 | 3/1967 | Guthrie | 128—292 |
| 3,236,370 | 2/1966 | Pereny et al. | 128—132 |
| 3,030,957 | 4/1962 | Melges | 128—132 |
| 3,154,789 | 11/1964 | Lewis | 2—104 |
| 3,260,260 | 7/1966 | Questel | 128—132 |
| 3,300,786 | 1/1967 | Rosenvold et al. | 2—2 |

OTHER REFERENCES

Aseptic Barriers, Archives of Surgery, August 1963, vol. 87; pp. 288–295.

RICHARD A. GAUDET, Primary Examiner

G. F. DUNNE, Assistant Examiner

PO-1050
(5/69)

UNITED STATES PATENT OFFICE
CERTIFICATE OF CORRECTION

Patent No. RE. 27,710 Dated July 24, 1973

Inventor(s) Frederick J. Melges

It is certified that error appears in the above-identified patent and that said Letters Patent are hereby corrected as shown below:

Column 1, line 37, for "gal" read -- gall -- .
Column 4, line 31, for "way" read -- may -- ; line 75, for "saving" read -- having -- .

Signed and sealed this 25th day of December 1973.

(SEAL)
Attest:

EDWARD M.FLETCHER,JR.
Attesting Officer

RENE D. TEGTMEYER
Acting Commissioner of Patents